United States Patent
Orosco et al.

(10) Patent No.: US 10,818,381 B2
(45) Date of Patent: Oct. 27, 2020

(54) ELECTRONIC MEDICAL RECORD INTEGRATION SYSTEM AND METHODS

(71) Applicant: Datica, Inc., Minneapolis, MN (US)

(72) Inventors: John Orosco, Johnston, IA (US); Jeremy E. Pierotti, Minneapolis, MN (US)

(73) Assignee: Datica, Inc., Minneapolis, MN (US)

(*) Notice: Subject to any disclaimer, the term of this patent is extended or adjusted under 35 U.S.C. 154(b) by 972 days.

(21) Appl. No.: 15/186,241

(22) Filed: Jun. 17, 2016

(65) Prior Publication Data
US 2017/0161435 A1      Jun. 8, 2017

Related U.S. Application Data

(60) Provisional application No. 62/264,714, filed on Dec. 8, 2015.

(51) Int. Cl.
*G16H 10/60* (2018.01)
*G16H 40/20* (2018.01)
*G06F 16/84* (2019.01)
*G06F 16/958* (2019.01)

(52) U.S. Cl.
CPC ............. *G16H 10/60* (2018.01); *G06F 16/86* (2019.01); *G06F 16/986* (2019.01); *G16H 40/20* (2018.01)

(58) Field of Classification Search
CPC ....... G16H 10/60; G06F 16/86; G06F 16/986; G06F 19/00
See application file for complete search history.

(56) References Cited

U.S. PATENT DOCUMENTS

| | | | |
|---|---|---|---|
| 7,752,035 | B2 | 7/2010 | Oon |
| 8,583,694 | B2 | 11/2013 | Siegel et al. |
| 8,650,045 | B2 | 2/2014 | Baldock et al. |
| 8,918,385 | B1 | 12/2014 | Ansari et al. |
| 9,996,664 | B2 | 6/2018 | Lloyd et al. |
| 2011/0178821 | A1 | 7/2011 | Smith |

(Continued)

FOREIGN PATENT DOCUMENTS

WO    2015/137703 A1    9/2015

OTHER PUBLICATIONS

International Search Report and Written Opinion for International Application No. PCT/US2016/065432, dated Feb. 17, 2017, 10 pages.

(Continued)

*Primary Examiner* — Michael Tomaszewski
*Assistant Examiner* — Mohmad Muqueeth
(74) *Attorney, Agent, or Firm* — Fredrikson & Byron, P.A.

(57) ABSTRACT

Methods and systems for obtaining reference data from one or more EMR systems are described. A universal API request may be sent from an external application server to middleware. The universal API request may be translated into an EMR-specific request via the middleware. The EMR-specific request may be sent to the selected EMR system. An EMR-specific response may be received from the one or more EMR systems at the middleware, being generated by the selected EMR systems. The EMR-specific response may be translated into a universal API response via the middleware. The universal API response may be received at the external application server from the middleware.

24 Claims, 5 Drawing Sheets

(56) References Cited

U.S. PATENT DOCUMENTS

| | | | |
|---|---|---|---|
| 2012/0215560 A1* | 8/2012 | Ofek | G06Q 10/10 |
| | | | 705/3 |
| 2013/0030838 A1 | 1/2013 | Myers et al. | |
| 2013/0185087 A1 | 7/2013 | Merkin | |
| 2014/0249854 A1* | 9/2014 | Moore | G16H 15/00 |
| | | | 705/3 |
| 2015/0088549 A1 | 3/2015 | Moore et al. | |

OTHER PUBLICATIONS

Julie Creswell, "Doctors Find Barriers to Sharing Digital Medical Records," The New York Times (http://nyti.ms/Zo1Tuk) Sep. 30, 2014, 5 pages.

* cited by examiner

ELECTRONIC MEDICAL RECORD INTEGRATION SYSTEM AND METHODS

FIELD

This disclosure generally relates to devices, systems, and methods for automating the identification and listing of the metadata and customizable build structure (reference data) of various disparate and incompatible electronic medical record systems and providing results that can be used by external software applications to facilitate data exchange.

BACKGROUND

Nearly every medium or large health care provider organization uses multiple specialized information systems to manage patient care delivery, revenue cycle processes, and supporting activities. Electronic medical record (EMR) applications (and their associated databases) commonly serve as one of the most important health care information systems. Because EMRs record data about virtually every patient-focused activity, they contain complicated data structures. One type of critical data is commonly known as "build data" or "reference data," because it includes reference tables for core data entities commonly referenced by transactional records, such as lab test structures, facilities, encounter types, pharmacy formularies, assessment forms, and other data entities that are referenced by nearly every recorded activity in the EMR. As an example, when a physician enters into the EMR an order for a lab test, that order record itself references other database records that describe frequently used characteristics of such an order: available lab tests to be ordered, the facility (clinic or hospital location) at which the patient was seen when the physician placed the order, the encounter type related to the order (e.g., office visit, inpatient stay, outpatient surgery), and other related characteristics. Each of these characteristics is known as "reference data" or "build data." For an external application to interact effectively with an EMR—for example, if an external application is to allow a physician to enter a lab test order that will be transmitted to the EMR—the external application must have an up-to-date record of the reference data in the EMR. If such an external application is missing records of available lab tests, a physician cannot order those lab tests. And while certain reference data (such as hospital room and bed numbers) change infrequently, reference tables for other entities (such as lab tests that may be ordered, or pharmaceuticals that are part of a hospital's core formulary) change more often. If the EMR has replaced its "Outpatient Surgery" encounter type with an "Ambulatory Surgery" encounter type—and the external application does not have the new Ambulatory Surgery record and has not retired the Outpatient Surgery record—the order transmitted to the EMR will fail.

Without the invention, the "mapping" of "reference data" records between external applications and EMRs is a manual process, performed laboriously by information technology workers who manually maintain "mapping tables," which are text or spreadsheet-type files that correlate reference data from the system of record (the EMR) to similar reference data in an external application. Because mapping tables are manually maintained, they are prone to error (both errors of commission and errors of omission). The invention automates mapping of—and the process of accurately maintaining—reference data records between the EMR and external applications that utilize the invention. Further, the invention makes it unnecessary for administrators of an external application to have knowledge of where or how the reference data is stored in the EMR (the system of record), because the invention provides a standardized mechanism for querying for reference data from any supported EMR software platform, and the invention always returns the results in a standardized format. Thus this invention builds on the U.S. Provisional Application No. 62/264,714 by the same inventors. Finally, the invention supports efficient maintenance of changed reference data records by keeping a log of the reference data request history by each external application, and allowing the return of only those reference data records that have changed in the system of record since the external application's previous request.

SUMMARY

In one aspect, the disclosure is directed toward a method for obtaining reference data from one or more EMR systems. The method includes sending a universal API request from an external application server to middleware. The universal API request includes parameters specifying a reference data category and a selected EMR system and may be formatted in a unified data model independent of the selected EMR system. The universal API request is translated into an EMR-specific request via the middleware recognized by the selected EMR system. The EMR-specific request is sent to the selected EMR system. An EMR-specific response is received from the one or more EMR systems at the middleware, being generated by the selected EMR systems. The EMR-specific response is in a format recognized by the selected EMR system and includes reference data related to the specified reference data category. The EMR-specific response is translated into a universal API response via the middleware. The universal API response is formatted in the unified data mode and includes the reference data formatted in the unified data model. The universal API response is received at the external application server from the middleware.

In another aspect, the method includes sending a universal API request from an external application server to middleware. The universal API request including parameters specifying a reference data category and a selected EMR system and may be formatted in a unified data model not recognized by the EMR systems. The universal API request is analyzed to determine which of the EMR systems is the selected one of the EMR systems. The universal API request is translated into an EMR-specific request via the middleware. The EMR-specific request is formatted to be recognized by the selected EMR systems and not by the other EMR systems. The EMR-specific request is sent to the selected EMR system and not to other EMR systems. An EMR-specific response is received from the EMR systems at the middleware, t being generated by the selected EMR systems. The EMR-specific response is in a format recognized by the selected EMR systems and includes reference data related to the specified reference data category. The EMR-specific response is translated into a universal API response via the middleware. The universal API response is formatted in the unified data model and includes the reference data formatted in the unified data model. The universal API response is received at the external application server from the middleware.

In another aspect, the disclosure is directed toward a system for obtaining reference data from one or more EMR systems. Middleware is configured to receive a universal API request from an external application server. The universal API request includes parameters specifying a reference data category and a selected EMR system and is formatted in a unified data model independent of the selected EMR system. The middleware is configured to translate the universal API request into an EMR-specific request. The EMR-specific request is recognized by the selected EMR system. The middleware is configured to send the EMR-specific request to the selected EMR systems. The middleware is also configured to receive an EMR-specific response from the one or more EMR systems. The EMR-specific response is generated by the selected EMR system and is in a format recognized by the selected EMR system. The EMR specific response includes reference data defined by the specified reference data category. The middleware is configured to translate the EMR-specific response into a universal API response. The universal API response is formatted in the unified data model. The EMR-specific response includes the reference data formatted in the unified data model. The middleware is configured to send the universal API response to the external application server.

BRIEF DESCRIPTION OF THE DRAWINGS

The following drawings illustrate particular embodiments and therefore do not limit the scope of the invention. The drawings are intended for use in conjunction with the explanations in the following detailed description. Embodiments will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing exemplary embodiments. Examples are provided for selected elements, and all other elements employ that which is known to those of ordinary skill in the field of the invention. Those skilled in the art will recognize that many of the noted examples have a variety of suitable alternatives.

Figure 1:
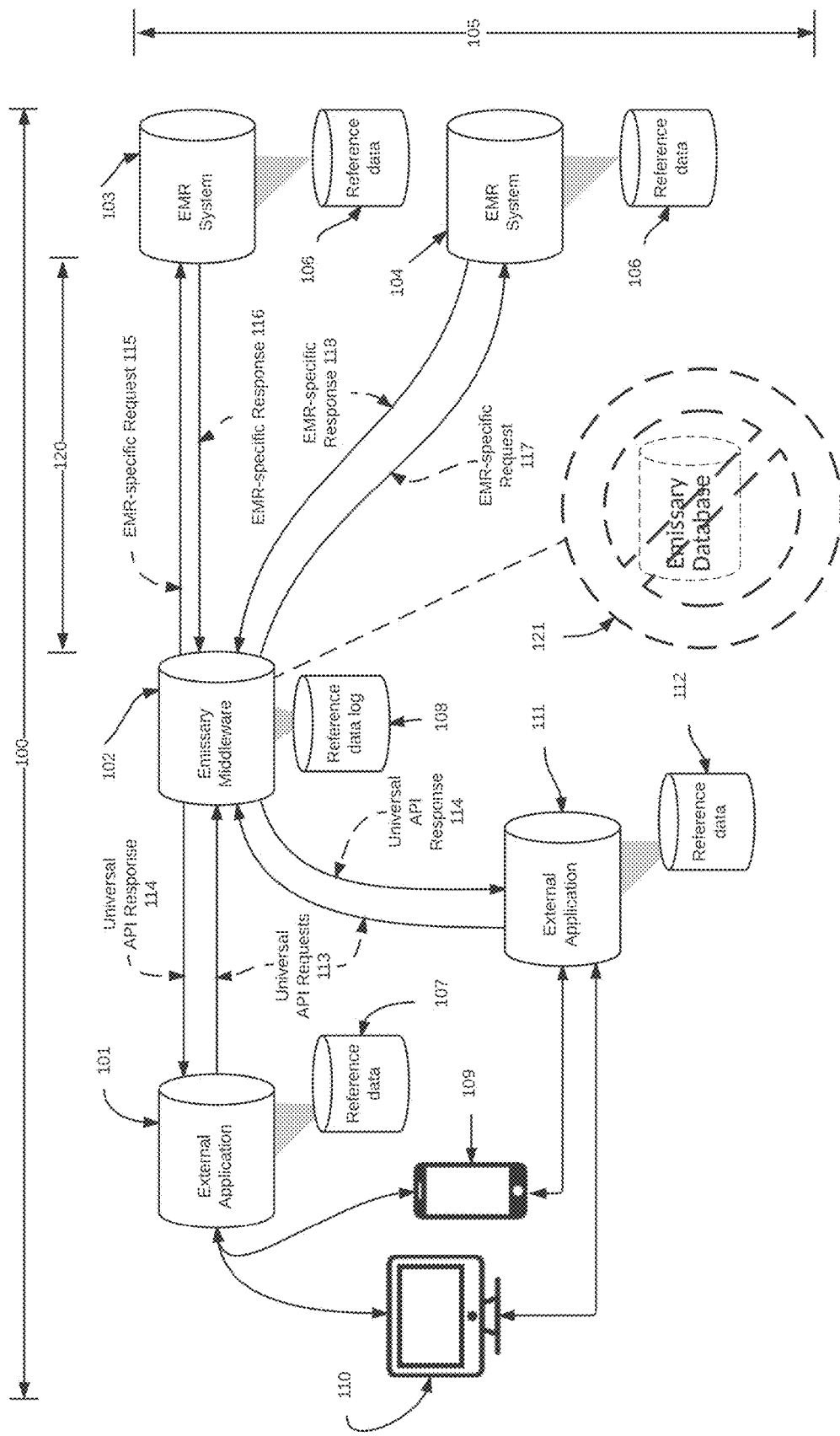
FIG. 1 is a high-level schematic depiction of a system according to an embodiment.
Figure 2:
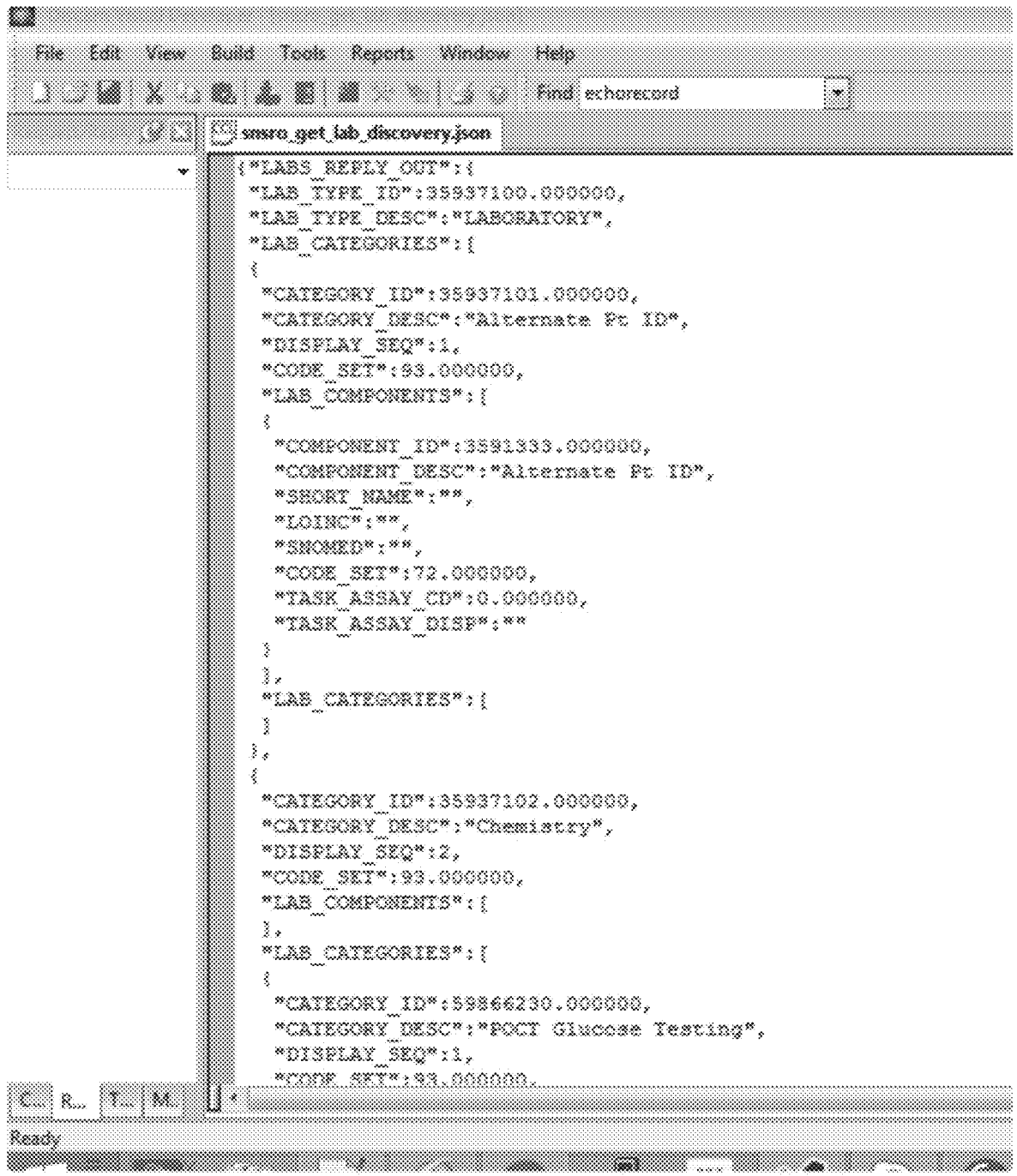
FIG. 2 is an example of a standardized response provided by the invention (in this case, a portion of the representation of available lab tests to be ordered) to assist software developers who will create applications using the invention.

FIG. 1 is a high-level schematic depiction of an application system 100 according to some embodiments of the invention. The application system 100 includes external applications 101 and 111 (software developed and provided separately from middleware 102 and EMR systems 105), middleware 102, and EMR systems 105. The external applications 101 and 111 may be applications provided by a distinct vendor (unaffiliated with the middleware 102 or EMR systems 105 vendors) that provides a data entry and retrieval interface for authorized users. For example, the external application 101 could be an application accessible through the Internet that presents clinic scheduling options for patients on a user computer 110 or user tablet or smartphone 109.

The external application 101 communicates with the middleware 102. In general, the external application 101 requests reference data from one of the EMR systems 105 by sending a Universal API Request 113 to the middleware 102. The Universal API Request 113 is a web services query defined by middleware 102 as a standard format irrespective of the application or data structure of the target EMR systems 105. Middleware 102 transforms the Universal API Request(s) 113 to EMR-specific Request 115 (and perhaps also EMR-specific request 117) compatible with the applicable EMR system and communicates the request(s) to one or more of the EMR systems 105. According to some embodiments, the EMR systems 105 could consist of more or fewer EMR systems than those illustrated in FIG. 1. In this example, the queried EMR system 103 then communicates results for the query—valid clinic locations—to the middleware 102 as an EMR-specific Response 116. The middleware 102 takes the response 116 received from the EMR system 103 and transforms the response into the Universal API Response 114 format and sends that response (a JSON object or XML file) to the external application 101. In this manner the external application 101 is able to request reference data from one or more EMR systems 105 without having any knowledge of the proprietary data structures or EMR-specific Request formats (115 and 117) and EMR-specific Response formats (116 and 118) that would otherwise be necessary for external application 101 to obtain the reference data in a structured electronic format. The external application 101 generally utilizes the results to provide valid clinic location options for the user to select as part of appointment scheduling functionality in a user-friendly interface on devices like a user user tablet or smartphone 109 or computer 110.

According to some embodiments, the external application 101 may require frequent updates to reference data changes in the EMR systems 105 via the middleware 102 and it would be inefficient as part of each query for the external application 101 to retrieve the complete list of values for each type of reference data requested. For example, the health care provider organization may have a collection of pre-visit questionnaire templates stored within EMR system 103, and these questionnaires are provided to patients on external application 101 based on the type of encounter being scheduled (e.g., annual physical exam, well-baby visit, post-surgical follow-up exam).

It is important that external application 101 maintain an accurate representation of the questionnaire templates within its own database, so that appropriate questionnaires can be presented to patients when scheduling appointments. For the external application 101 to update the questionnaire templates in its own database, it would be inefficient to query the entire list of questionnaire templates stored in EMR system 103. Therefore, the external application 101 would use Universal API Request 113 to query the middleware 102 for changes or additions to the questionnaire templates. Middleware 102 would use an EMR-specific Request format 113 to obtain records from EMR system 103 and, based on the reference data log 108, would return to external application 101 only the changes, deletions, or additions to the questionnaire templates that were made since the previous query submitted by the external application 101. Further, middleware 102 would store a timestamp representing the date, time, and scope of data returned by EMR system 103 to middleware 102. With this log, the next time that external application 101 requested a record of changes to the same scope of reference data in EMR system 103, middleware 102 would utilize the reference data log 108 in order to refine the EMR-specific Request 115 transmitted to EMR system 103.

According to some embodiments, middleware 102 would use an EMR-specific Request format 113 to obtain records from EMR system 103 based on a timestamp in reference data log 108 indicating the most recent query submitted by the external application 101. Middleware 102 would return to external application 101 only the changes, deletions, or additions to the questionnaire templates that were made since the previous query submitted by the external application 101. Further, middleware 102 would store a timestamp representing the date, time, and scope of data returned by EMR system 103 to middleware 102. The next time that external application 101 requested a record of changes to the same scope of reference data in EMR system 103, middleware 102 would utilize the timestamp of the most recent response received from EMR system 103 in order to refine the EMR-specific Request 115 transmitted to EMR system 103.

According to some embodiments, a health care provider organization may utilize multiple EMR systems 105, such as EMR system 103 in its hospitals and EMR system 104 in its ambulatory clinics. While the native functionality of EMR systems 103 and 104 are inconsistent as to access for types of reference data, an external application 101 would—using the invention—consistently be able to obtain data from EMR systems 103 and 104 for all supported reference data types. For example, the external application 101 may perform calculations and present information to health-care providers based on a complex patient acuity scoring system. The third-party server 101 would query the middleware 102 to obtain the reference data necessary from each EMR systems 103 and 104 to perform such calculations, such as facility structure (hospital, department, and clinic listings), medication orders, lab test orders and other data about available treatments provided to patients. This would enable external application 101 to correlate information—such as similar or identical lab test and medication order options—across EMR systems 103 and 104 as part of its patient acuity scoring analytics functionality. By combining the reference data with patient-specific condition and treatment information, the external application 101 would perform analytics using the returned data and present results to a health-care provider, for example on a user computer 110.

According to some embodiments, the middleware software 102 may receive commands from multiple external applications such as external applications 101 and 111. In one embodiment, a hospital computer 110 that displays a user interface connected to a single EMR system may embed a web viewer capable of connecting to other EMR systems through using application system 100. This could be used to retrieve patient information that is located on multiple EMR systems 103 and 104 operated by the health care provider organization. In this embodiment, the external application 111 would send a request to and receive reference data back from the middleware 102. Upon receipt of the data, the external application 111 would automatically modify its user interface so that the embedded web viewer would display patient information accurately from other EMR systems within the current EMR.

The middleware 102 incorporates connectors 120, which are web services that facilitate direct, real-time communication with EMR systems 105. EMR-specific Requests 115 and 117, and the EMR-specific Responses 116 and 118, are examples of such connectors. The application system 100 has a unique, dedicated connector tailored to each EMR system. The middleware also includes custom-built connector to enable real-time communication with an EMR system produced by MEDITECH, which does not provide its own connector. This custom-built connector 110 is the only means of retrieving real-time data from the MEDITECH EMR system 106.

The middleware 102 receives real-time data from EMR systems 105 or writes to EMR systems 105 by querying said systems in response to discrete commands transmitted from external applications 101 and 111. Existing systems that query or write to EMR systems cannot maintain perfect synchronization with EMR systems 105 because they copy data periodically from EMR systems into a database 121. This applies to the reference data stored in EMR systems 105 in addition to the transactional data specific to individual patients or activity records. Because the application system 100 makes real-time queries, it does not include a database 121 made by compiling data from each EMR system at a specific time and making that database 121 available for query.

Obtaining real-time data and writing data in real time has substantial advantages over existing systems. Because application system 100 does not store patient information, there is a lower risk of data breach given that there are no duplicative systems holding sensitive information. Additionally, existing systems may not provide complete or accurate information. For example, if a patient attended an appointment on a Monday morning and a different health care provider queried that patient's "encounters" using the middleware 102 later that same day, the middleware 102 would retrieve this new data point when it queried the EMR systems 105 and include the data point in the user's results. If the application system 100 relied instead on a database 121 compiled from all EMR systems 105, the application system 100 would only retrieve the new data point representing the patient's latest appointment if queried after the database 121 was updated to include the new data by querying the appropriate EMR system. As patients often have multiple appointments within a short time period, and the schedules for updating a central database vary, there may be differences or data gaps between data in the EMR systems 105 and database 121.

Figure 5:
FIG. 5 is an illustration of reference data queries arranged in a list of categories as they might appear in the application documentation.

Reference data queries available in application system 100 are arranged in categories, such as "Labs" or "Medications." An embodiment of these categories is illustrated in FIG. 5, which depicts a list of categories as they might appear in application documentation. Within each category are commands and reference data elements related to that category. For example, document structure is listed under the category "Documents" while flowsheet structures are listed under the category "Flowsheets" within the middleware 102. A user of the application system 100 may submit a command for specific reference data categories. The middleware 102 correlates each data element queried by the user to an analogous reference data type in each of the EMR systems 105. In the example of the data element "Documents," the middleware 102 maps "Documents" and its related command to the analogous Document categories reference data as defined in the databases for each of the EMR systems 105. "Flowsheets" may correlate to a data element "flowsheets" in one EMR system, and to "assessments" in another.

Figure 3:
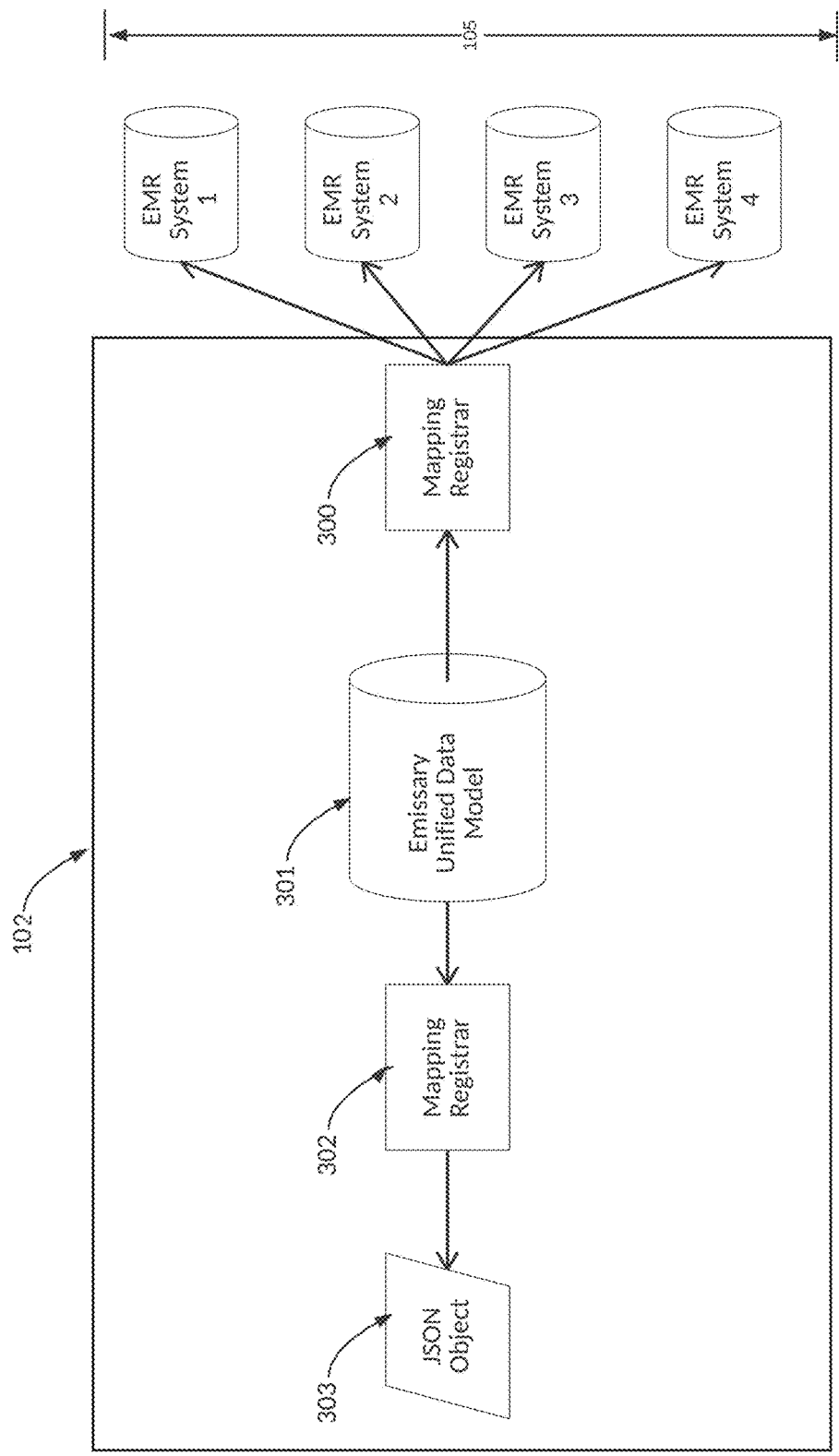
FIG. 3 is a depiction of a process for transferring data received in different formats from various EMR systems into a unified format accessible to users.

FIG. 3 is a high-level schematic that illustrates the use of mapping registrars in the middleware 102 to convert commands and data elements into formats recognizable by the EMR systems 105 and the user of the application system 100. Upon the middleware 102 receiving a command from third-party server 101 or 111, it uses mapping registrar 300 to convert said commands into commands recognizable by each EMR system.

FIG. 3 also illustrates the unified data model 301, which converts data via mapping registrar 302. To enable users to process data elements retrieved from different EMR systems in the same way, each data element must be provided to users in an identical format. The schema of data formats is referred to as unified data model 301. The middleware 102 translates data received from the EMR systems 105 using customized mapping registrar 300 into the unified data model 301. In order to return the data to the user in a standard format, the middleware 301 then converts the reformatted data using mapping registrar 302 into a JSON object, XML file, or other similar item 303.

The unified data model 301 only includes data elements that are available in one or more EMR systems 105. If the EMR system queried contains no defined corollary to a given data element, a query of that EMR system for the term will return no results. For example, if a user queries the application system for laboratory orders or results, a query of an EMR system that contains no data element correlated to the data element "LOINC Code" (a standardized nomenclature for clinical and laboratory observations) will return no results.

Figure 4:
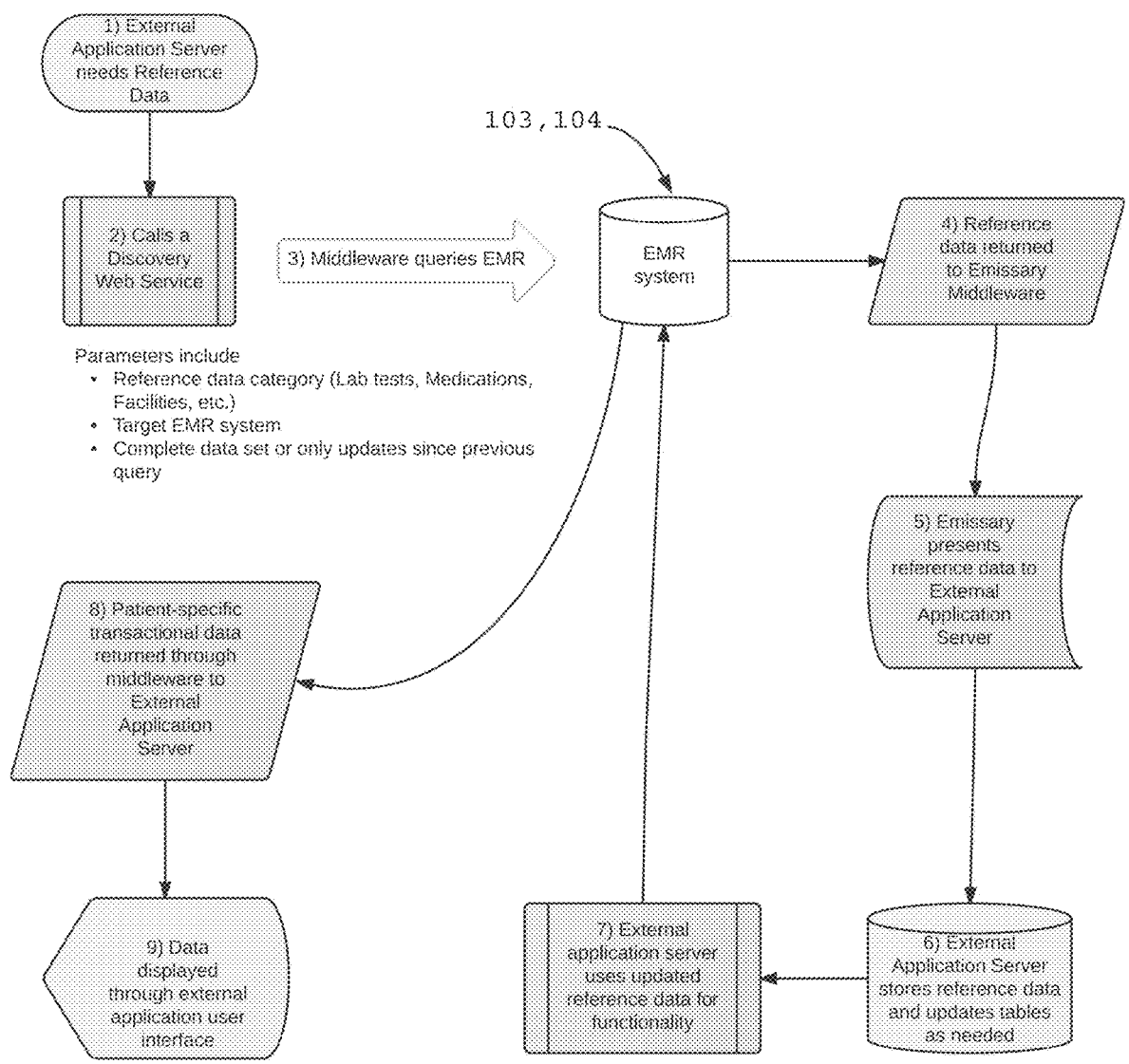
FIG. 4 is a flow diagram of a method for searching an EMR system and retrieving complete results of a type of reference data of according to an embodiment.

FIG. 4 is a flowchart demonstrating how the application system 100 queries the individual EMR systems 105 to obtain reference data. The external application 101 initiates a Discovery command in step 1.

All commands sent to the middleware 102 by external application 101 or 111 must include a EMR ID because middleware 102 queries a specific EMR within available EMR systems 105 for reference data. Queries sent to a Lab Discovery endpoint provided by the middleware 102 would return lab test order structure data for a specific EMR within available EMR systems 105.

The middleware 102 receives the GET command string representing the Discovery command from the external application 101 or 111 in step 2. In step 3, the middleware 102 evaluates a parameter in the GET command to determine which of the EMR systems 105 is specified as the subject of the query. Further, middleware 102 evaluates a parameter in the GET command to determine whether external application 101 or 111 is requesting a complete data set of the reference data (e.g., all lab test order structure data) or only the updates to the lab test order structure data since the external application's previous request.

The middleware 102 sends the formatted request 115 (or 117) directly to the specified EMR system. In step 4, the specified EMR system receives the request and sends the requested reference data as an EMR-specific response 116 (or 118) to the middleware 102. Based on the parameters indicated in the GET string (step 2), the middleware 102 in step 5 returns the reference data in a standard format to the external application 101 or 111. If the external application 101 or 111 requests a complete set of reference data (e.g., all available lab tests that may be ordered) in step 2, it will receive the complete catalog from middleware 102. If the external application 101 or 111 requests only incremental updates made to the subject EMR system 105 since the external application's prior inquiry, middleware 102 returns only the records that have changed since the prior query for the same reference data.

In step 5, the middleware further packages the data into a standardized JSON object or XML file 303, so that reference data elements are presented in a standardized form to the external application 101 or 111 irrespective of the target EMR system 103 or 104.

In step 6, the external application 101 of 111 updates its own reference tables to match the values provided by the subject EMR system 105.

This allows, in step 7, the external application 101 or 111 to perform its functionality accurately, such as presenting valid choices (such as an accurate and updated list of clinic locations for a patient scheduling application, or available lab tests to be ordered for a physician-focused patient care application) to users of the application(s) as they interact with the external application using a handheld device 109 or computer 110. In steps 8 and 9, the user interacts with the external application user interface to perform the functionality offered by the external application.

Various examples have been described. These and other examples are within the scope of claims to be provided in this application.

The invention claimed is:

1. A method of obtaining reference data from one or more EMR systems comprising:
    receiving, by middleware, a universal API request from a first external application server, the universal API request including parameters specifying a reference data category and specifying a first EMR system of the one or more EMR systems, the universal API request being formatted in a unified data model independent of the first EMR system;
    translating, by the middleware, the universal API request into an EMR-specific request, the EMR-specific request being recognized by the first EMR system;
    sending, by the middleware, the EMR-specific request to the first EMR system;
    receiving, by the middleware, an EMR-specific response from the first EMR system, the EMR-specific response being generated by the first EMR system, the EMR-specific response being in a format recognized by the first EMR system, the EMR-specific response including reference data related to the specified reference data category;
    determining, by the middleware and based on a reference data log, a most recent request for the reference data by the first external application server, wherein the reference data log includes a record of dates of previous requests, times of previous requests, and scope of the reference data included in previous EMR-specific responses;
    altering, by the middleware and based on the records in the reference log, the EMR-specific response to include only changes, deletions, or additions to the reference data since the most recent request for the reference data by the first external application server;
    translating, by the middleware, the altered EMR-specific response into a universal API response, the universal API response being formatted in the unified data model, the universal API response including only the changes, deletions, or additions to the reference data since the most recent request for the reference data by the first external application server and formatted in the unified data model; and
    sending, by the middleware, the universal API response to the first external application server.

2. The method of claim 1, wherein the translating of the universal API request into the EMR-specific request includes:

comparing, by the middleware, the EMR-specific request with the reference data log; and refining, by the middleware, the EMR-specific request based on the reference data log, the reference data log storing the reference data of EMR-specific responses received from previous EMR-specific requests.

3. The method of claim 1, wherein the translating of the universal API request into the EMR-specific request includes refining, by the middleware, the EMR-specific request based on the timestamp of EMR-specific responses received from previous EMR-specific requests in the reference data log.

4. The method of claim 1, wherein upon the receiving of the universal API response, the external application server updates a database of the external application server to reflect the reference data included within the universal API response.

5. The method of claim 1, wherein the middleware does not include a database compiled from all EMR systems.

6. The method of claim 1, wherein the universal API request comprises a web services query.

7. The method of claim 1, wherein the middleware includes one or more web service connectors, each web service connector tailored to communicate directly with one of the one or more EMR systems.

8. The method of claim 1, wherein the reference data category includes commands and reference data.

9. The method of claim 1, wherein the middleware includes a mapping registrar, the mapping registrar correlating formatted elements in the unified data model to elements in the one or more EMR systems.

10. The method of claim 8, further comprising:
translating, by the middleware, the universal API request into the EMR-specific request via the mapping registrar; and
translating, by the middleware, the EMR-specific response into the universal API response via the mapping registrar.

11. The method of claim 1, wherein the universal API request further includes parameters specifying whether the universal API response should include a complete data set of the reference data or only changes, deletions, or additions to the reference data since a previous universal API request.

12. A method of obtaining reference data from EMR systems comprising:
receiving, by middleware, a universal API request from a first external application server, the universal API request including parameters specifying a reference data category and specifying a first EMR system of the EMR systems, the universal API request being formatted in a unified data model not recognized by the EMR systems;
analyzing, by the middleware, the universal API request to determine which of the EMR systems is the first EMR system;
translating, by the middleware, the universal API request into an EMR-specific request, the EMR-specific request being recognized by the first EMR system; and not recognized by the other EMR systems of the EMR systems;
sending, by the middleware, the EMR-specific request to the first EMR system and not to other EMR systems;
receiving, by the middleware, an EMR-specific response from the first EMR system, the EMR-specific response being generated by the first EMR system, the EMR-specific response being in a format recognized by the first EMR system, the EMR-specific response including reference data related to the specified reference data category;
determining, by the middleware and based on a reference data log, a most recent request for the reference data by the first external application server, wherein the reference data log includes a record of dates of previous requests, times of previous requests, and scope of the reference data included in previous EMR-specific responses;
altering, by the middleware and based on the records in the reference log, the EMR-specific response to include only changes, deletions, or additions to the reference data since the most recent request for the reference data by the first external application server;
translating, by the middleware, the altered EMR-specific response into a universal API response, the universal API response being formatted in the unified data model, the universal API response including only the changes, deletions, or additions to the reference data since the most recent request for the reference data by the first external application server and formatted in the unified data model; and
sending, by the middleware, the universal API response to the first external application server.

13. The method of claim 12, wherein upon the receiving of the universal API response, the external application server updates a database of the external application server to reflect the reference data included within the universal API response.

14. A system for obtaining reference data from one or more EMR systems, comprising:
middleware configured to:
receive a universal API request from a first external application server, the universal API request including parameters specifying a reference data category and specifying a first EMR system of the one or more EMR systems, the universal API request being formatted in a unified data model independent of the first EMR system,
translate the universal API request into an EMR-specific request, the EMR-specific request being recognized by the first EMR system,
send the EMR-specific request to the first EMR system,
receive an EMR-specific response from the first EMR system, the EMR-specific response being generated by the first EMR system, the EMR-specific response being in a format recognized by the first EMR system, the EMR-specific response including reference data related to the specified reference data category,
determine, based on a reference data log, a most recent request for the reference data by the first external application server, wherein the reference data log includes a record of dates of previous requests, times of previous requests, and scope of the reference data included in previous EMR-specific responses;
alter, based on the records in the reference log, the EMR-specific response to include only changes, deletions, or additions to the reference data since the most recent request for the reference data by the first external application server;
translate the altered EMR-specific response into a universal API response, the universal API response being formatted in the unified data model, the universal API response including only the changes, deletions, or additions to the reference data since the most recent request for the reference data by the first external application server and formatted in the unified data model, and send the universal API response to the first external application server.

15. The system of claim 14, wherein the middleware being configured to translate the universal API request into the EMR-specific request includes the middleware being configured to:

compare the EMR-specific request with the reference data log, and refine the EMR-specific request based on the reference data log, the reference data log storing the reference data of EMR-specific responses received from previous EMR-specific requests.

16. The system of claim 14, wherein the middleware being configured to translate the EMR-specific response into the universal API response includes the middleware being configured to:

refine the EMR-specific response based on the timestamp of EMR-specific responses received from previous EMR-specific requests in the reference data log.

17. The system of claim 14, wherein upon the receiving of the universal API response, the external application server updates a database of the external application server to reflect the reference data included within the universal API response.

18. The system of claim 14, wherein the reference data category includes commands and reference data.

19. The system of claim 14, wherein the middleware includes a mapping registrar, the mapping registrar correlating formatted elements in the unified data model to elements in the one or more EMR systems.

20. The system of claim 19, wherein the middleware is further configured to:

translate the universal API request into the EMR-specific request via the mapping registrar, and translate the EMR-specific response into the universal API response via the mapping registrar.

21. The system of claim 14, wherein the universal API request further includes parameters specifying whether the universal API response should include a complete data set of the reference data or only changes, deletions, or additions to the reference data since a previous universal API request.

22. The method of claim 1, wherein the universal API request comprises a first universal API request, wherein the universal API response comprises a first universal API response, and wherein the method further comprises:

receiving, by the middleware, a second universal API request from a second external application server, the second universal API request including parameters specifying a second reference data category and specifying a second EMR system of the one or more EMR systems, the second universal API request being formatted in the unified data model independent of the second EMR system, the second EMR system being different than the first EMR system, and the second external application server being different than the first external application server;

translating, by the middleware, the second universal API request into a second EMR-specific request, the second EMR-specific request being recognized by the second EMR system;

sending, by the middleware, the second EMR-specific request to the second EMR system;

receiving, by the middleware, a second EMR-specific response from the second EMR system, the second EMR-specific response being generated by the second EMR system, the second EMR-specific response being in a format recognized by the second EMR system, the second EMR-specific response including reference data related to the second specified reference data category;

translating, by the middleware, the second EMR-specific response into a second universal API response, the second universal API response being formatted in the unified data model, the universal API response including the reference data formatted in the unified data model;

sending, by the middleware, the second universal API response to the second external application server.

23. The method of claim 1, wherein the reference data category comprises a particular intake questionnaire template, and wherein the reference data comprises one or more updates to the particular intake questionnaire template since a most recent request by the first external application server for the particular intake questionnaire template.

24. The method of claim 1, wherein the universal API request comprises a first universal API request, wherein the universal API response comprises a first universal API response, and wherein the method further comprises:

receiving, by the middleware, a second universal API request from the first external application server, the second universal API request including parameters specifying the reference data category and specifying a second EMR system of the one or more EMR systems, the second universal API request being formatted in the unified data model independent of the second EMR system, and the second EMR system being different than the first EMR system;

translating, by the middleware, the second universal API request into a second EMR-specific request, the second EMR-specific request being recognized by the second EMR system;

sending, by the middleware, the second EMR-specific request to the second EMR system;

receiving, by the middleware, a second EMR-specific response from the second EMR system, the second EMR-specific response being generated by the second EMR system, the second EMR-specific response being in a format recognized by the second EMR system, the second EMR-specific response including reference data related to the specified reference data category;

translating, by the middleware, the second EMR-specific response into a second universal API response, the second universal API response being formatted in the unified data model, the universal API response including the reference data formatted in the unified data model;

sending, by the middleware, the second universal API response to the first external application server.

* * * * *